United States Patent [19]

Baumann et al.

[11] 4,224,253
[45] Sep. 23, 1980

[54] NOVEL BICYCLIC SCENTS

[75] Inventors: Manfred Baumann, Mannheim; Werner Hoffmann, Neuhofen, both of Fed. Rep. of Germany

[73] Assignee: BASF Aktiengesellschaft, Fed. Rep. of Germany

[21] Appl. No.: 937,267

[22] Filed: Aug. 28, 1978

[30] Foreign Application Priority Data

Sep. 20, 1977 [DE] Fed. Rep. of Germany ....... 2742185

[51] Int. Cl.$^2$ .................... C07C 33/05; C07C 47/34; C07C 121/48; C07C 69/74
[52] U.S. Cl. ................................. 568/445; 260/464; 560/120; 568/820; 585/21; 585/357; 252/522 R
[58] Field of Search ......... 568/820; 260/598, 666 PY, 260/464; 560/120

[56] References Cited

U.S. PATENT DOCUMENTS

| | | | |
|---|---|---|---|
| 3,662,007 | 5/1972 | Fanta et al. | 568/820 |
| 3,662,008 | 5/1972 | Kretschmar et al. | 260/666 PY X |
| 3,673,256 | 6/1972 | Pieper et al. | 260/598 |
| 3,673,261 | 6/1972 | Kretschmar et al. | 560/120 X |
| 4,010,213 | 3/1977 | Naegeli | 260/598 X |
| 4,128,509 | 12/1978 | Schleppnik | 568/820 X |

FOREIGN PATENT DOCUMENTS 2719976 11/1978 Fed. Rep. of Germany .

OTHER PUBLICATIONS

Kretschmar, et al., Tetrahedron Letters, 1970, pp. 41-44.
Christenson, et al., J. Org. Chem., 44, 1979, pp. 2012-2018.
Demole et al., Helv. Chim. Acta, 59 (1976), pp. 737-747.
Trippett, Quarterly Reviews, 17 (1963), pp. 406-440.
Buddrus, Angew. Chem., 80 (1978), pp. 535-536.
Brieger, Tetrahedron Letters, 28 (1963), pp. 1949-1951.

*Primary Examiner*—Joseph Paul Brust
*Attorney, Agent, or Firm*—Keil & Witherspoon

[57] ABSTRACT

Novel 2-methylene-3-methyl-3-(1',3'-pentadien-1'-yl)-bicyclo-[2,2,1]-heptanes substituted in the 4'-position by methyl, alkoxycarbonyl, formyl, hydroxymethyl or cyano are obtained by reacting the novel aldehyde 2-methylene-3-methyl-3-formyl-bicyclo-[2,2,1]-heptane with 3-methyl-, 3-alkoxycarbonyl- or acetalized 3-formyl-2-butene-1-triarylphosphorylidene under the conditions of a Wittig reaction, with or without hydrolytic cleavage of the acetal group, or hydrolytic cleavage of the acetal group followed by reduction of the formyl group to the hydroxymethyl group, or hydrolytic cleavage of the acetal group, reaction of the aldehyde with a hydroxylammonium salt, and dehydration of the resulting oxime.

The novel compounds are distinguished by interesting scent characteristics.

3 Claims, No Drawings

NOVEL BICYCLIC SCENTS

The present invention relates to novel compounds of the general formula I

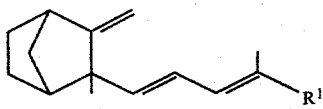

where $R^1$ is —$CH_2OH$, —CHO, —$COOCH_3$, —$COOC_2H_5$, —CN or —$CH_3$ and to processes for their preparation.

The novel compounds possess interesting scent characteristics and hence constitute an enrichment of the range of valuable fully synthetic scents and hence also an enrichment of the art.

The compound of the formula I, where R is —$CH_2OH$, has a particularly interesting fragrance. The carbon skeleton of the novel compounds resembles the skeleton of a sought-after natural fragrance material obtained from sandalwoods, viz. β-santalol

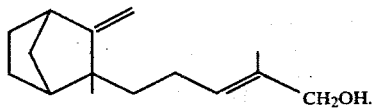

The compound of the formula I, where R is —$CH_2OH$, could be described as dehydro-β-santalol.

The novel compounds of the general formula I, where $R^1$ is —$CH_3$, —$COOCH_3$ or —$COOC_2H_5$ may advantageously be prepared by a method wherein the aldehyde of the formula II

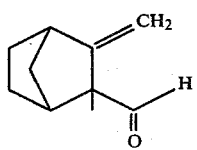

is reacted, under the conditions of a Wittig reaction, with a phosphorylide of the general formula III

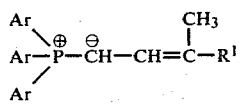

where the Ar radicals are identical or different aryl, especially phenyl or tolyl, or cyclohexyl, and $R^1$ has the above meaning.

The novel compound of the general formula I, where $R^1$ is —CHO, may be obtained by a method wherein the aldehyde of the formula II

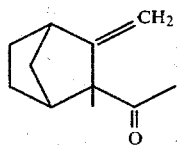

is reacted, under conditions of a Wittig reaction, with a phosphorylide of the general formula III

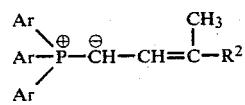

where $R^2$ is the acetal group

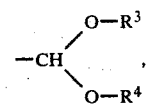

$R^3$ and $R^4$ being an aliphatic hydrocarbon radical of 1 to 4 carbon atoms or $R^3$ and $R^4$ together being an ethylene or propylene radical which may be substituted by one or more alkyl of 1 to 4 carbon atoms, preferably methyl, and the Ar radicals are identical or different aryl, especially phenyl or tolyl or cyclohexyl, and the resulting acetal is hydrolyzed under acid conditions in the conventional manner.

The compounds of the formula I, where $R^1$ is —$CH_2OH$, may be obtained by a method wherein (A) the aldehyde of the formula II

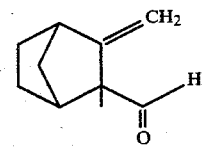

is reacted, under the conditions of a Wittig reaction, with a phosphorylide of the general formula III

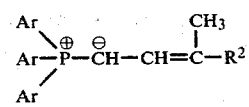

where $R^2$ is an acetal group

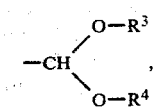

$R^3$ and $R^4$ being an aliphatic hydrocarbon radical of 1 to 4 carbon atoms or $R^3$ and $R^4$ together being an ethylene or propylene radical which may be substituted by one or more alkyl of 1 to 4 carbon atoms, preferably methyl, and the Ar radicals are identical or different aryl, especially phenyl or tolyl or cyclohexyl.

(B) the resulting acetal is hydrolyzed under acid conditions in the conventional manner and (C) the resulting aldehyde of the general formula I is reduced with $LiAlH_4$ or by the Meerwein-Ponndorf method with aluminum isopropylate.

The compound of the formula I, where $R^1$ is —CN, may be obtained by a method wherein (A) the aldehyde II

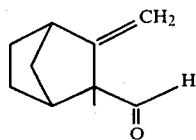

is reacted, under the conditions of a Wittig reaction, with a phosphorylide of the general formula III

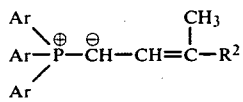

where $R^2$ is an acetal group

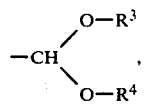

$R^3$ and $R^4$ being an aliphatic hydrocarbon radical of 1 to 4 carbon atoms or $R^3$ and $R^4$ together being an ethylene or propylene radical which may be substituted by one or more alkyl of 1 to 4 carbon atoms, especially methyl, and the Ar radicals are identical or different aryl, especially phenyl or tolyl or cyclohexyl, (B) the resulting acetal is hydrolyzed under acid conditions in the conventional manner, (C) the resulting aldehyde of the general formula I is converted to the oxime by means of a hydroxylammonium salt, in the conventional manner, and (D) the resulting oxime is dehydrated in the conventional manner.

The essential reaction step in the preparation of the novel bicyclic scents, which is common to all cases, is the Wittig reaction between the aldehyde of the formula II and a phosphorylide of the general formula III.

The aldehyde II, (2-methylene-3-methyl-3-formyl-bicyclo-[2,2,1]-heptane) has hitherto neither been synthesized nor characterized. A publication in Helv. Chim. Acta 59 (1976), 738 states that certain experimental indications suggest that the bicyclic teresantalal II also occurs in sandalwood oil. The aldehyde II can be obtained from the novel compound 2-chloromethyl-3-methyl-3-formylbicyclo-[2,2,1]-heptane (described in German Patent Application No. P 27 19 976, which however does not constitute a prior publication) by elimination of HCl, whilst protecting the formyl group by acetalizing. The compound boils at 74°–78° C./0.2 mm Hg.

The phosphorylides may be prepared in the conventional manner, for example by treating the phosphonium salts, on which they are based, with strong bases. Further details are to be found, inter alia, in the summary by Tripett (Quart. Reviews, 17 (1963), 406 et seq.).

An advantageous method of carrying out the reaction according to the invention is to prepare the phosphorylide from the corresponding phosphonium salt directly in the solvent envisaged for the Wittig synthesis, and if appropriate even in the presence of the aldehyde to be converted. The requisite phosphonium salts can be prepared by a simple conventional method, namely reaction of the corresponding alkyl halides, especially the corresponding alkyl chlorides, with triarylphosphines or tricyclohexylphosphine, especially with triphenylphosphine.

The bases conventionally used for Wittig syntheses may be used as the strong bases for the preparation of the phosphorylides. Examples include alkali metal hydroxides, alkali metal hydrides, alkali metal amides, alkali metal alcoholates, alkaline earth metal alcoholates, phenyllithium and butyl-lithium, sodium alcoholates and potassium alcoholates being preferred.

Ethylene oxide (see Angew. Chem. 80 (1968), 535 et seq.) and excess phosphorylide can, under certain conditions, also take the place of the strong base.

Suitable solvents for the preparation of the phosphorylides, and for the Wittig reaction, are the solvents conventionally used for Wittig syntheses, for example aliphatic or aromatic hydrocarbons, eg. hexane, octane, cyclohexane, benzene, toluene and xylene and their halogenation products, alcohols, eg. methanol, ethanol, isopropanol, butanols, hexanols, cyclohexanol and cyclooctanol as well as glycols, ethers, eg. diisopropyl ether, ethylene glycol dimethyl ether, tetrahydrofuran, dimethyltetrahydrofuran and dioxane, or mixtures of these. Polar organic solvents, eg. methanol, ethanol, formamide, dimethylformamide, N-methylpyrrolidone, hexamethylphosphorotriamide, acetonitrile and dimethylsulfoxide, and mixtures of these solvents, are particularly suitable. The process of the invention can also be carried out in water or in aqueous mixtures.

The reaction according to the invention of the aldehyde II with the phosphorylidene III is advantageously carried out by introducing a phosphonium salt of the formula IV

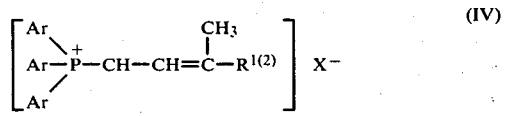

where X is chlorine, bromine or iodine and $R^1$ or $R^2$ and Ar have the above meanings, and about a stoichiometric amount of the aldehyde to be reacted, into a solvent and then adding about a stoichiometric amount of a strong base in portions to this suspension at from −20° to +70° C., preferably from 0° to 30° C., whilst stirring, with or without cooling, and introducing dry nitrogen. The reaction mixture is then kept at from 15° to 30° C., preferably at room temperature, for from 1 to 24 hours, preferably from 1 to 2 hours.

However, the reaction according to the invention can also be carried out by adding about the stoichiometric amount of a strong base to the solution of the phosphonium salt at the above temperature, then adding the aldehyde of the formula II to the phosphorylide solution obtained above, and thereafter allowing the reaction to finish as described above.

In total, from about 1 to 1.2 moles of base are used per mole of phosphonium salt for the above reaction. The reaction mixture is worked up in the conventional manner by separating the reaction product from the triarylphosphine oxide or tricyclohexylphosphine oxide formed, for example by extraction and distillation, with or without subsequent preparative chromatography.

The acid hydrolysis of the acetal obtained by the Wittig reaction of the aldehyde II with the phosphorylidene III containing an acetal group is carried out in the conventional manner. For example, the acetal is advantageously treated with from 0.01 to 1 mole, per mole of acetal, of a mineral acid, eg. sulfuric acid or hydrochloric acid, or an organic acid, eg. formic acid or p-toluenesulfonic acid or acetic acid, in the form of a solution of from 1 to 20 percent strength, and the batch is heated, with thorough mixing, for from 0.5 to 5 hours, preferably from 2 to 3 hours, at from 10° to 50° C.

For the hydrolysis, it is advisable to add a solubilizing agent to the reaction mixture. Particularly suitable solubilizing agents are lower aliphatic alcohols, eg. methanol, ethanol and propanol, as well as cycloaliphatic ethers, eg. tetrahydrofuran and dioxane. The aldehyde obtained can be isolated in the conventional manner, for example by extraction after gently neutralizing the reaction mixture, for example with an alkali metal bicarbonate or sodium carbonate, and distilling off the extractant.

The aldehyde of the formula I can be reduced in the conventional manner, by means of LiAlH$_4$, NaBH$_4$ or aluminum isopropylate, to give the alcohol of the formula I.

The solvent used for the reaction with LiAlH$_4$ is preferably an ether, eg. diethyl ether or tetrahydrofuran (THF). Advantageously, it is used in an amount of from about $\frac{1}{4}$ to 1 mole per mole of aldehyde. The reaction temperature is in general from room temperature to the reflux temperature of the solvent. The reaction time is from about 1 to 6 hours.

LiAlH$_4$ is introduced into an anhydrous solvent (in which it is partially dissolved and partially suspended). The carbonyl compound, in the relevant solvent, is slowly added to this mixture. Depending on the reactivity of the carbonyl compound, the reaction may have finished after stirring for several hours at room temperature, or may require heating for several hours.

Excess LiAlH$_4$ is destroyed by carefully adding an alcohol, eg. ethanol. The organic phase is washed with water, dried and concentrated. The reaction product is purified in the conventional manner, for example by distillation.

The reaction with NaBH$_4$ is in general carried out in protic solvents, eg. water or ethanol, the latter being preferred. Advantageously, it is used in an amount of from about $\frac{1}{4}$ to 1 mole per mole of carbonyl compound. The reaction is in general carried out at room temperature; the reaction time is from about 2 to 12 hours.

The reaction mixture is worked up in the conventional manner, for example by decomposing the residue with a dilute acid and then extracting with a solvent.

For the reduction of the aldehyde of the formula I with aluminum isopropylate (Meerwein-Ponndorf-Verley reduction), the solvent used is anhydrous isopropyl alcohol. To carry out the reduction, the Al isopropylate is introduced into isopropanol and the carbonyl compound is added to this mixture. From $\frac{1}{2}$ to 2 moles of Al isopropylate are used per mole of carbonyl compound. On heating the mixture, acetone is formed, and this is distilled off through a column. The reaction is in general carried out at from about 60° to 120° C. and the reaction time is from about 30 to 60 minutes.

When no further acetone is formed, the residue is decomposed with dilute acid and the product is isolated, for example by extraction with a solvent.

To convert the aldehyde of the formula I to the oxime, it is advantageous to add to the carbonyl compound an equivalent amount, or a slight excess, of a hydroxylammonium salt, eg. hydroxylammonium chloride or hydroxylammonium sulfate, in water or alcohol or in a mixture of these.

The reaction is in general carried out at from room temperature to the boiling point of the solvent. Bases, eg. hydroxides, carbonates, bicarbonates, acetates or the like are added in order to neutralize the acid liberated and give a pH, in the reaction mixture, of from about 4 to 5.

To work up the mixture, water is added and the oxime is isolated by extraction with a solvent.

A dehydration of the oxime is also carried out in the conventional manner by reaction with a dehydrating agent, eg. an anhydride or acid chloride or P$_2$O$_5$, or by thermal elimination of water. Advantageously, the oxime is heated for several hours with a large excess of acetic anhydride. The reaction is in general carried out at from room temperature to the boiling point of the particular solvent. The reaction time is from about 1 to several hours. The solvent used is either the oxime itself or an aprotic solvent, for example a chlorohydrocarbon, eg. CH$_2$Cl$_2$ or CHCl$_3$; a hydrocarbon, eg. toluene or xylene, or an ether, eg. dioxane or tetrahydrofuran. The mixture is generally worked up by decomposition with water and extraction with a solvent.

The novel bicyclic compounds possess interesting scent characteristics and hence broaden the range of available valuable fully synthetic fragrance materials.

EXAMPLE 1

73 g (0.2 mole) of 3-methyl-2-butene-1-triphenylphosphonium chloride are suspended in 200 ml of THF. 0.22 mole of butyl-lithium, in the form of 138 ml of a 1.6 N solution of butyl-lithium in hexane, is added dropwise, whilst cooling. The contents of the flask turn deep red. 29 g (0.2 mole) of the aldehyde 2-methylene-3-methyl-3-formyl-bicyclo-[2,2,1]-heptane in 50 ml of THF are then added dropwise and the reaction mixture is heated for 6 hours at 50° C.

The solution is then concentrated, the residue is extracted by boiling with petroleum ether and the solution in the latter solvent is washed with aqueous methanol, dried and concentrated. This leaves a residue of 38.6 g.

Subsequent distillation gives 3 g of the aldehyde starting material and 30.6 g of 2-methylene-3-methyl-3-(4'-methyl-1',3'-pentadien-1'-yl)-bicyclo-[2,2,1]-heptane (II) boiling at 65° C./0.01 mm Hg; $n_D^{25} = 1.5260$. The IR and NMR spectra confirm the structure; the NMR spectrum indicates a mixture of the exo and endo compounds. The yield is 82%, based on aldehyde converted. Scent: pleasantly woody.

EXAMPLE 2

85 g (0.2 mole) of 3-ethoxycarbonyl-2-butene-1-triphenylphosphonium chloride are reacted, by the method described in Example 1, with 138 ml of a 1.6 N butyllithium solution (corresponding to 1.1 times the molar amount) in hexane and then with 29 g (0.2 mole) of 2-methylene-3-methyl-3-formyl-bicyclo-[2,2,1]-heptane. In addition to 14.3 g of unconverted aldehyde, 6.2 g of 2-methylene-3-methyl-3-(4'-ethoxycarbonyl-1',3'-pentadien-1'-yl)-bicyclo-[2,2,1]-heptane boiling at 150° C./0.01 mm Hg are obtained; $n_D^{25} = 1.5312$. The yield is 24%, based on aldehyde converted.

Scent: sweet, fruity, aniseed-like.

EXAMPLE 3

(a) 90.5 g (0.2 mole) of 3-(4'-methyl-1',3'-dioxan-2'-yl)-2-butene-1-triphenylphosphonium chloride are reacted, by the method described in Example 1, with 138 ml of a 1.6 N butyl-lithium solution in hexane and then with 29 g of the aldehyde II. In addition to 19 g of unconverted aldehyde, 18.6 g of 2-methylene-3-methyl-3-[4'-(4''-methyl-1'',3''-dioxan-2''-yl)1',3'-pentadien-1'-yl]-bicyclo-[2,2,1]-heptane, boiling at 160° C./0.01 mm Hg, are obtained; $n_D^{25} = 1.5233$. The IR and NMR spectra confirm the structure. The yield is 93%, based on aldehyde converted.

(b) 27 g of the acetal obtained as described in 3 (a) are stirred with 50 ml of 10 percent strength aqueous $H_2SO_4$ and 50 ml of dioxane for 2 hours at 20° C. The reaction mixture is then diluted with 50 ml of water and extracted with ether. The ether extracts are washed neutral with bicarbonate solution, dried and concentrated.

10 g of 2-methylene-3-methyl-3-(4'-formyl-1',3'-pentadien-1'-yl)-cicyclo-[2,2,1]-heptane, boiling at 103°–106° C./0.2 mm Hg, are obtained; the IR and NMR spectra confirm the structure. The yield is 50%, based on aldehyde II employed.

Scent: fresh, woody.

EXAMPLE 4

9.2 g (0.0426 mole) of the aldehyde obtained as described in 3 (b) are dissolved in 20 ml of ethanol and the solution is added dropwise to a mixture of 0.6 g (0.015 mole) of $NaBH_4$ and 50 ml of ethanol. The reaction mixture is stirred for 4 hours at 20° C. and is then concentrated, water is added and the mixture is rendered slightly acid with dilute $H_2SO_4$ and is extracted with ether. The resulting organic phase is dried and concentrated. On subsequent distillation, 6.4 g of 2-methylene-3-methyl-3-(4'-hydroxymethyl-1',3'-pentadien-1'-yl)-bicyclo-[2,2,1]-heptane boiling at 130° C./0.08 mm Hg are obtained. In a refrigerator, the product solidifies to a wax. The IR and NMR spectra confirm the structure. The yield is 70%, based on acetal employed.

Scent: balsamy, woody, mild.

EXAMPLE 5

6 g of hydroxylammonium chloride, 6 g of Na acetate and 40 g of water are added to 9 g of the bicyclic aldehyde obtained as described in Example 3 (b) and the resulting mixture is heated for 30 minutes at 60° C. It is then cooled, 50 ml of water are added, the mixture is extracted with ether and the combined ether phases are concentrated. 20 g of acetic anhydride are added to the resulting crude oxime and the mixture obtained is refluxed for 2 hours. Water is then added, the mixture is extracted with ether and the ether phase obtained is neutralized, dried and concentrated. The residue is purified by chromatography on silica gel, using a 3:1 petroleum ether/ether mixture as the eluent. 5.4 g of 2-methylene-3-methyl-3-(4'-cyano-1',3'-pentadien-1'-yl)-bicyclo-[2,2,1]-heptane, boiling at 100°–105° C./0.2 mm Hg, are obtained. The yield is 61%, based on aldehyde employed. The scent resembles that of the aldehyde of the formula I, but is somewhat fruitier.

We claim:

1. A compound of the formula I

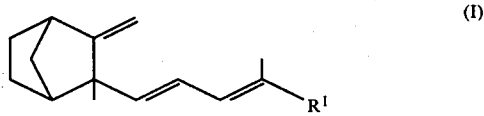

(I)

where $R^1$ is $-CH_2OH$ or $-CHO$.

2. A compound as set forth in claim 1 wherein $R^1$ is $-CH_2OH$.

3. A compound as set forth in claim 1 wherein $R^1$ is $-CHO$.

* * * * *